United States Patent [19]
Ratron

[11] Patent Number: 5,676,702
[45] Date of Patent: Oct. 14, 1997

[54] ELASTIC DISC PROSTHESIS

[75] Inventor: Yves-Alain Ratron, Grenoble, France

[73] Assignee: Tornier S.A., Saint-Ismier, France

[21] Appl. No.: 566,132

[22] Filed: Dec. 1, 1995

[30] Foreign Application Priority Data

Dec. 16, 1994 [FR] France .................... 94 15435

[51] Int. Cl.$^6$ .................................................. A61F 2/44
[52] U.S. Cl. ........................................................ 623/17
[58] Field of Search ................... 623/17, 47, 52, 623/53, 55; 403/291, 392; 267/141, 152

[56] References Cited

U.S. PATENT DOCUMENTS

| 2,433,356 | 4/1947 | Mathis | 623/54 |
| 5,062,859 | 11/1991 | Naeder | 623/55 |
| 5,156,632 | 10/1992 | Wellershaus | 623/55 |
| 5,306,308 | 4/1994 | Gross et al. | 623/17 |
| 5,320,644 | 6/1994 | Baumgartner | |
| 5,458,642 | 10/1995 | Beer et al. | 623/17 |

FOREIGN PATENT DOCUMENTS

1710015-A1  2/1992  U.S.S.R. ............. A61B 17/58

Primary Examiner—John G. Weiss
Assistant Examiner—John M. Black
Attorney, Agent, or Firm—Dowell & Dowell

[57] ABSTRACT

An elastic intervertebral disc prosthesis comprising two opposite plates joined together by partitions capable of deforming elastically as a function of the load applied on the prosthesis.

12 Claims, 2 Drawing Sheets

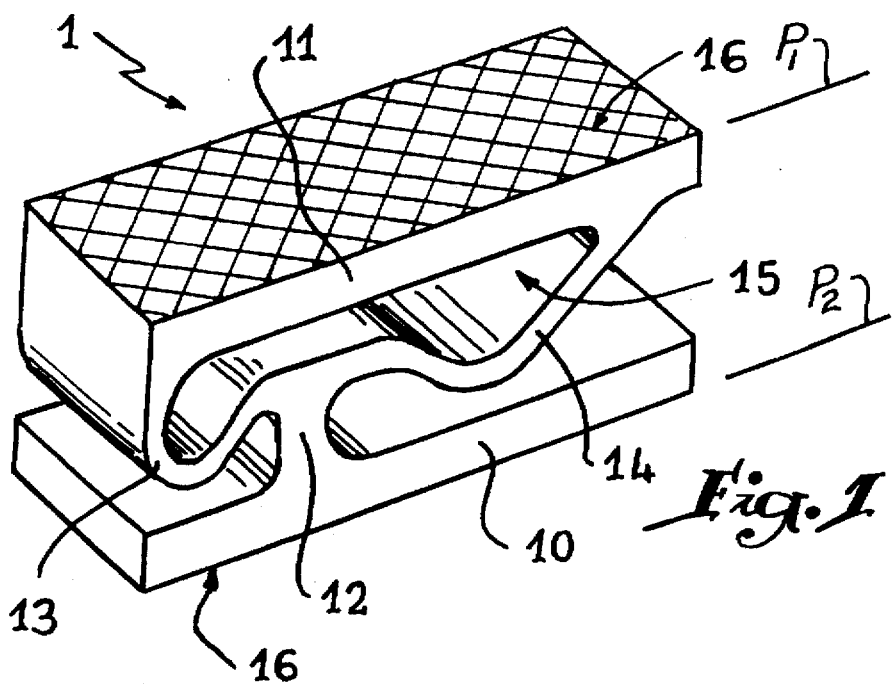
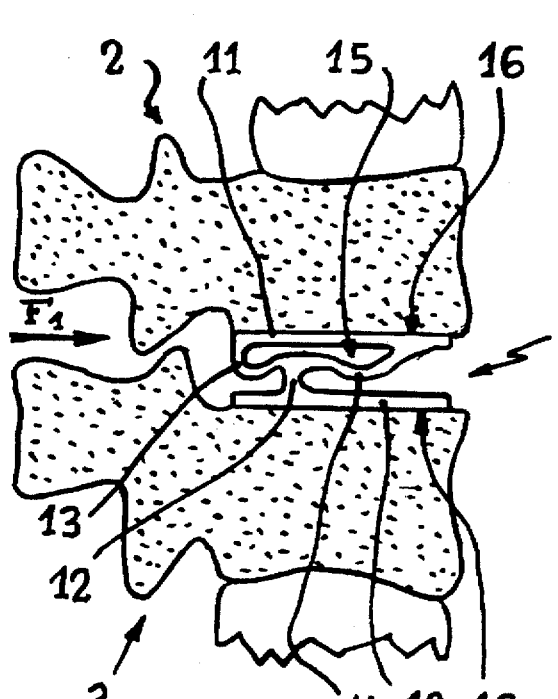
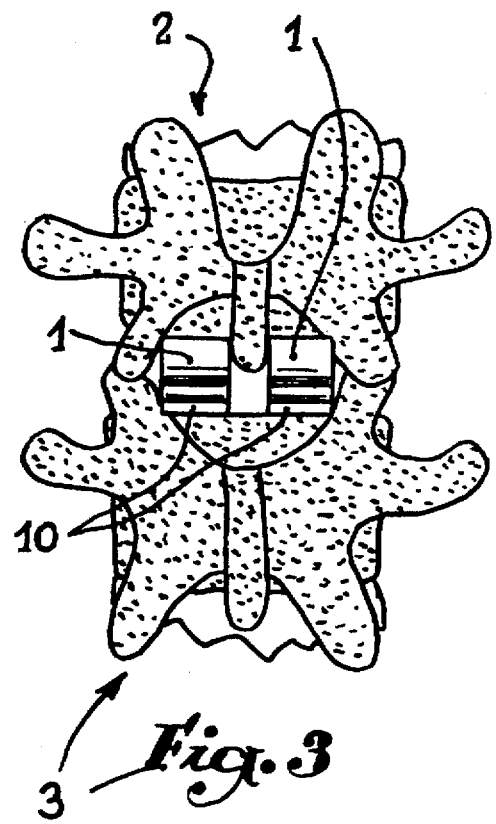

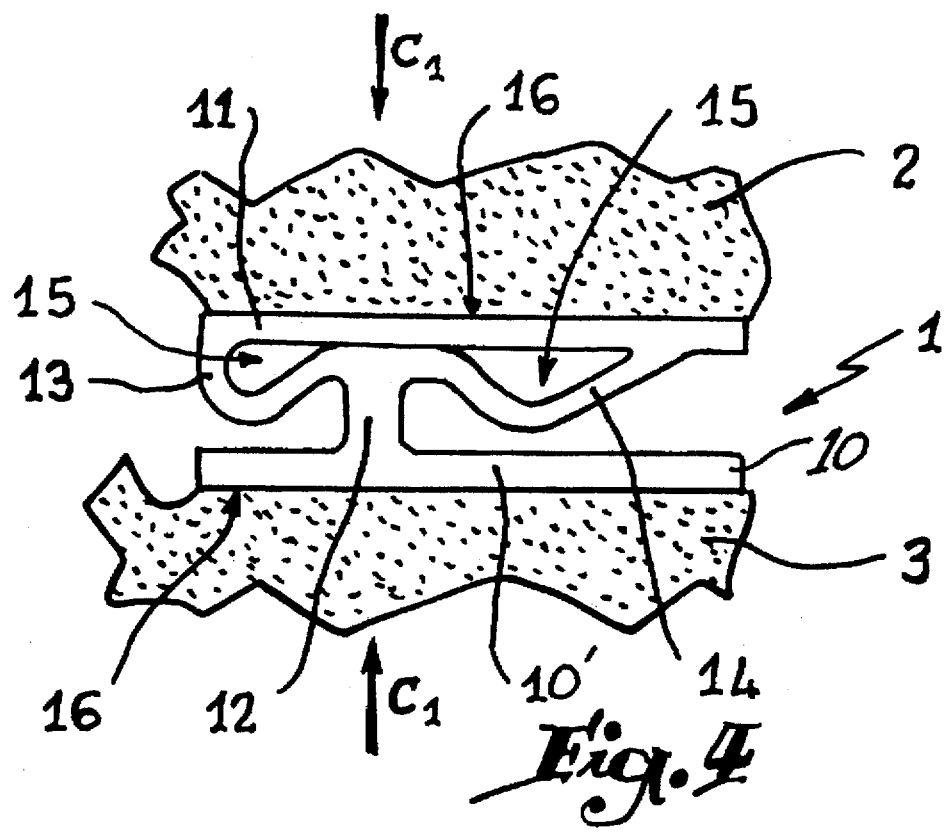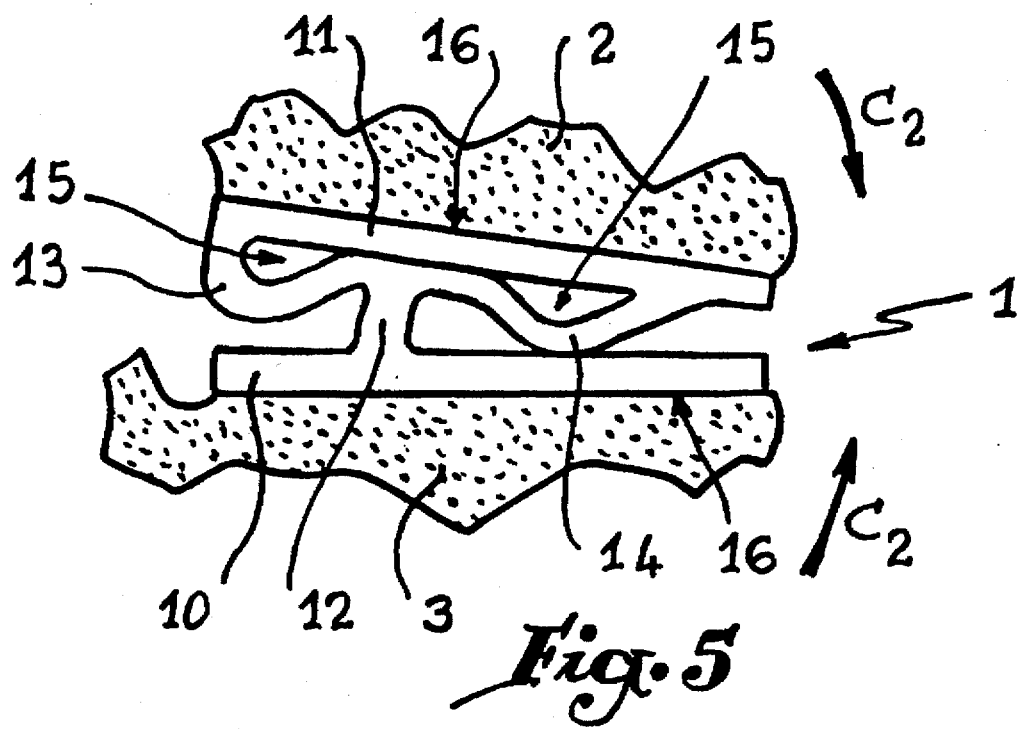

ELASTIC DISC PROSTHESIS

BACKGROUND OF THE INVENTION

1. Field of the Invention

The present invention relates to an elastic disc prosthesis intended totally or partially to replace a damaged disc between two vertebrae of a spine.

2. History of the Related Art

Prostheses of this type are known, which are constituted by two plates each provided with anchoring flanges and threaded orifices for fixation thereof in the vertebrae after ablation of the damaged disc. The two plates are separated by an articulation member constituted by a spherical cap with cylindrical base. One of the plates comprises a spherical bearing surface of the same diameter as the cap, while the other plate is provided to receive the cylindrical base for axial retention of the cap.

Such a discal prosthesis ensures only the axial displacements of the vertebrae with respect to one another, but it does not allow the vertical displacements to be dampened when the vertebrae are under load. In addition, it presents the drawback of being introduced and positioned by the anterior route, which creates difficulties and discomfort for the patient.

It is a particular object of the present invention to overcome these drawbacks.

SUMMARY OF THE INVENTION

The disc prosthesis according to the invention comprises two opposite plates joined together by partitions capable of elastically deforming as a function of the load applied on the prosthesis.

The first plate of the disc prosthesis according to the invention comprises a vertical partition which extends respectively on each side of its principal axis in curved partitions which are joined or integral with the second plate, defining a free or open space whose volume may vary as a function of the load applied.

BRIEF DESCRIPTION OF THE DRAWINGS

The invention will be more readily understood on reading the following description with reference to the accompanying drawings, in which:

FIG. 1 is a perspective view illustrating the intervertebral disc prosthesis according to the present invention.

FIGS. 2 and 3 are views showing the positioning of the disc prosthesis between two adjacent vertebrae of a spine.

FIG. 4 is a side view showing the prosthesis when the vertebrae are subjected to a moderate load.

FIG. 5 is a side view illustrating the prosthesis when the vertebrae are subjected to a heavy load.

DESCRIPTION OF PREFERRED EMBODIMENT

Referring now to the drawings, FIGS. 1 to 3 firstly show a disc prosthesis 1 intended to replace, totally or partially, a vertebral disc located between two adjacent vertebrae 2 and 3.

The disc prosthesis 1 comprises two opposite plates 10 and 11 which are disposed in two parallel horizontal planes $P_1$ and $P_2$ when it is at rest, i.e. when it is not subjected to any load, either moderate or heavy.

The first plate 10 comprises a vertical partition 12 of short height which is offset laterally with respect to the middle 10' of the plate. The vertical partition 12 extends outwardly respectively on each side of its principal axis in secondary partitions 13, 14 which are joined or integral with the second plate 11.

Partitions 13 and 14 have curved profiles of different radii so as to define with plate 11 a free or open space 15.

The curvature of each partition 13 and 14 is convex downwardly, i.e. in the direction of plate 10.

Those faces of plates 10 and 11 which are in contact with the vertebrae 2 and 3 are covered with roughness 16 to ensure adequate anchoring in the osseous tissue.

The shaping of partitions 12, 13 and 14 allows elastic displacement of plate 10 with respect to plate 11 depending on the load applied from one of the plates on the other.

The disc prosthesis 1 is constituted by a single piece made of metallic material sufficiently elastic to dampen the different loads to which the vertebrae are subjected.

It will be noted that the surgical treatment for replacing a vertebral disc located between two vertebrae 2 and 3 will generally involve the placing of two disc prostheses 1 according to the present invention, one on either side of the spinal canal (FIGS. 2 and 3). The disc prostheses 1 are introduced between the two vertebrae 2 and 3 by the posterior route in the direction of arrow F1 as shown in FIG. 2.

FIG. 4 shows the disc prosthesis 1 when the vertebrae 2 and 3 are subjected to a moderate load. It is ascertained that, under the effect of the load $C_1$, the partitions 13 and 14 undergo an elastic deformation bringing the free end of partition 12 in abutment against plate 11. The rigidity or suppleness of such deformation is controlled by the shape and thickness of partitions 13 and 14, as well as by the nature of the material chosen. The elastic deformation of partitions 12 and 14 leads to a considerable reduction in the volume of the free space 15, enabling the load $C_1$ to be dampened.

FIG. 5 shows the disc prosthesis 1 when the vertebrae 2 and 3 are subjected to a greater load $C_2$. It is ascertained that, once the free space 15 is completely reduced, i.e. closed in two distinct spaces, the vertical partition 12 begins to deform laterally, bringing about a complementary elastic movement of the two plates 10 and 11. This complementary elastic movement consists in a tilting of the two plates 10 and 11 so that the partition 14 and more particularly its rounded profile, abuts on plate 10.

The center of rotation of such tipping, the rigidity or suppleness of this deformation are controlled by the shape and thickness of the vertical partition 12.

What is claimed is:

1. An intervertebral disc prosthesis for implanting between two vertebrae of a spine comprising, first and second plates having a middle portion, said first and second plates having oppositely oriented outer faces adapted to contact the vertebrae and having opposing inner surfaces, said first and second plates being oriented in generally parallel planes, said prosthesis having first and second elastically deformable partitions extending between and joining said first and second plates in such a manner as to exert differing reactive forces to said first and second plates when loads are applied to urge said first and second plates toward one another, said first and second partitions being oriented in planes which are generally not parallel to said parallel planes of said first and second plates, said second partition being solely resiliently compressible to apply a dampening reactive force to said first and second plates upon initial application of a first load to urge said first and second plates toward one another and said first partition being bendable to permit a tilting of said first and second plates relative to one another after initial compression of said second partition when a load greater than said first load is applied to urge said first and second plates toward one another, whereby said first and second partitions are oriented relative to said first and second plates such that said prosthesis exhibits different stiffness characteristics directly dependent on loads applied to said first and second plates when implanted between the vertebrae.

2. An intervertebral disc prosthesis for implanting between two vertebrae of a spine comprising, first and second plates having a middle portion, said first and second plates having oppositely oriented outer faces adapted to contact the vertebrae and having opposing inner surfaces, said first and second plates being oriented in generally parallel planes, said prosthesis having first and second elastically deformable partitions extending between and joining said first and second plates, said partitions being oriented in planes which are generally not parallel to said parallel planes of said first and second plates, said first partition including a first partition extending from said first plate toward said second plate and terminating in spaced relationship with respect to said second plate, and said second partition including a pair of secondary partitions extending outwardly from said first partition and on opposite sides thereof, said secondary partitions being joined to said second plate so as to define an open spaced therebetween whereby said first and second partitions are oriented relative to said first and second plates such that said prosthesis exhibits different stiffness characteristics directly dependent on loads applied to said first and second plates when implanted between the vertebrae.

3. The intervertebral disc prosthesis of claim 2 wherein said first partition is spaced from said middle portion of said first plate.

4. The intervertebral disc prosthesis of claim 3 wherein said secondary partitions have curved profiles having different radii.

5. The intervertebral disc prosthesis of claim 4 wherein said secondary partitions are convexly curved toward said first plate.

6. The intervertebral disc prosthesis of claim 5 wherein said first and second plates and said first and secondary partitions are integrally formed of a metallic material.

7. The intervertebral disc prosthesis of claim 6 wherein said outer faces of said first and second plates are roughened.

8. The intervertebral disc prosthesis of claim 2 wherein said secondary partitions have curved profiles having different radii.

9. The intervertebral disc prosthesis of claim 8 wherein said secondary partitions are convexly curved toward said first plate.

10. An intervertebral disc prosthesis for implanting between two vertebrae of a spine comprising, first and second plates having a middle portion, said first and second plates having oppositely oriented outer faces adapted to contact the vertebrae and having opposing inner surfaces, said first and second plates being oriented in generally parallel planes, said prosthesis having first and second elastically deformable partitions extending between and joining said first and second plates, said partitions being oriented in planes which are generally not parallel to said parallel planes of said first and second plates, said first and second plates and said first and second partitions being integrally formed of a metallic material, whereby said first and second partitions are oriented relative to said first and second plates such that said prosthesis exhibits different stiffness characteristics directly dependent on loads applied to said first and second plates when implanted between the vertebrae.

11. The intervertebral disc prosthesis of claim 10 wherein said outer faces of said first and second plates are roughened.

12. The intervertebral disc prosthesis of claim 10 wherein said first partition is spaced from said middle portion of said first plate.

* * * * *